United States Patent [19]
Weber et al.

[11] Patent Number: 4,668,517
[45] Date of Patent: May 26, 1987

[54] FURAZOLIDONE DOSAGE FORM

[75] Inventors: John B. Weber, Norwich, N.Y.; Jesus T. Covarrubias, Jeronimo, Mexico

[73] Assignee: Norwich Eaton Pharmaceuticals, Inc., Norwich, N.Y.

[21] Appl. No.: 720,120

[22] Filed: Apr. 4, 1985

[51] Int. Cl.$^4$ .......................... A61K 9/22; A61K 9/24
[52] U.S. Cl. ................................ 424/469; 424/486; 424/436
[58] Field of Search .................... 424/19-22

[56] References Cited

U.S. PATENT DOCUMENTS

| | | | |
|---|---|---|---|
| 2,928,770 | 3/1960 | Bardani | 167/82 |
| 3,325,365 | 6/1967 | Hotku et al. | 424/33 |
| 3,431,338 | 3/1969 | Munzel | 424/21 |
| 3,507,952 | 4/1970 | Rednick et al. | 424/22 |
| 3,548,052 | 12/1970 | Koh | 424/16 |
| 3,784,683 | 1/1974 | Prillig | 424/35 |
| 3,790,669 | 2/1974 | Gale | 424/120 |
| 3,870,790 | 3/1975 | Lowey et al. | 424/19 |
| 4,248,856 | 2/1981 | Guley et al. | 424/21 |
| 4,248,857 | 2/1981 | DeNesle et al. | 424/21 |
| 4,248,858 | 2/1981 | Guley et al. | 424/21 |
| 4,309,404 | 1/1982 | DeNeale et al. | 424/21 |
| 4,309,405 | 1/1982 | Guley et al. | 424/21 |
| 4,309,406 | 1/1982 | Guley et al. | 424/21 |
| 4,402,965 | 9/1983 | Wyburn-Mason | 424/272 |
| 4,432,966 | 2/1984 | Zeitoun et al. | 424/35 |

OTHER PUBLICATIONS

Rogers, G. S., G. B. Belloff, M. F. Paul, J. A. Yurchenco & G. Gever, "Furazolidone, a New Antimicrobial Nitrofuran", *Antibiotics and Chemotherapy*, vol. VI, No. 3 (Mar., 1956), pp. 231-242.

Carlson, J. R., S. A. Thornton, H. L. DuPont, A. H. West & J. J. Mathewson, "Comparative in vitro Activities of Ten Antimicrobial Agents Against Bacterial Enteropathogens", *Antimicrobial Agents and Chemotherapy*, vol. 24, No. 4 (Oct., 1983), pp. 509-513.

Benazet, F., L. LaCroix, C. Godard, L. Guillaume & J.-P Leroy, "Laboratory Studies of the Chemotherapeutic Activity and Toxicity of Some Nitroheterocycles", *Scandanavian Journal of Infective Diseases*, vol. 2, No. 2 (1970), pp. 139-143.

Sargeaunt, P. G. & W. H. R. Lumsden, "In vitro Sensitivity of *Entamoeba histolytica* to Furazolidone and Iodochlorhydroxyquin, Separate and Combined", *Transactions of the Royal Society of Tropical Medicine and Hygiene*, vol. 70, No. 1 (1976), pp. 54-56.

Vanhoof, R., H. Goossens, H. Coignau, G. Stas & J. P. Butzler, "Susceptibility Pattern of *Campylobacter jejuni* from Human and Animal Origins to Different Antimicrobial Agents", *Antimicrobial Agents and Chemotherapy*, vol. 21, No. 6 (Jun., 1982), pp. 990-992.

Wang, W.-L. L., L. B. Reller & M. J. Blaser, "Comparison of Antimicrobial Susceptibility Patterns of *Campylobacter jejuni* and *Campylobacter coli*", *Antimicrobial Agents and Chemotherapy*, vol. 26, No. 3 (Sep., 1984), pp. 351-353.

Gross, R. J., L. R. Ward, E. J. Threlfall, H. King & B. Rowe, "Drug Resistance Among Infantile Enteropathogenic *Escherichia coli* Strains Isolated in the United Kingdom", *British Medical Journal*, vol. 285, No. 6340 (Aug. 14, 1982), pp. 472-473.

Gross, R. J., E. J. Threlfall, L. R. Ward & B. Rowe, "Drug Resistance in *Shigella dysenteriae*, *S. flexneri* and *S. boydii* in England and Wales: Increasing Incidents of Resistance to Trimethoprim", *British Medical Journal*, vol. 288, No. 6419 (Mar. 10, 1984), pp. 784-786.

Panhotra, B. R. & B. Desai, "Resistant *Shigella dysenteriae*", *Lancet*, vol. 2, No. 8364 (Dec. 17, 1983), p. 1420.

Saxena, S. N., M. L. Mago, S. Ahuja & H. Singh, "*In vitro* Sensitivity of Salmonella Strains Isolated in 1978 to Ampicillin, Chloramphenicol and Furazolidone", *The Indian Journal of Medical Science*, vol. 35, No. 7 (Jul., 1981), pp. 147-152.

Agrawal, R., O. P. Ghai, Shriniwas, C. G. Domah & V. K. Paui, "Enterotoxigenic Klebsiella Associated Diarrhea in Children", *Indian Pediatrics*, vol. XVII, No. 9 (Sep., 1980), pp. 733-737.

Agarwal, S. K., V. K. Srivastava, G. C. Upadhyay, G. K. Malik & L. Tewari, "Shigellosis in Infants and Children", *Indian Pediatrics*, vol. 18, No. 5 (May, 1981), pp. 305-310.

Purohit, R. P., K. R. Joshi, M. C. Vyas & K. Banerjee, "Bacteriological Study of Acute Diarrhoeal Disorders in Adults in Jodhpur", *Rajasthan Medical Journal*, vol. XVIII, No. 4 (Oct., 1979), pp. 237-246.

DuPont, H. L., C. D. Ericsson, E. Galindo, L. V. Wood, D. Morgan, J. A. M. Bitsura and J. G. Mendiola, "Furazolidone Versus Ampicillin in the Treatment of Traveler's Diarrhea", *Antimicrobial Agents and Chemotherapy*, vol. 26, No. 2 (Aug., 1984), pp. 160-163.

Turner, A. C., "Traveler's Diarrhoea: Prevention by Chemoprophylaxis", *Scandanavian Journal of Gastroenterology*, vol. 84, Supplement (1983), pp. 107-110.

Lexomboon, U., "Antimicrobial Therapy in Diarrhoeal Diseases in Children", *Southeast Asian Journal of Tropical Medicine and Public Health*, vol. 13, No. 3 (Sep., 1982), pp. 418-423.

Gupta, S., S. Saxena & G. Srivastava, "Comparative Clinical Trial of Anti-Diarrhoeal Drugs", *Indian Pediatrics*, vol. XIV, No. 8 (1977), pp. 639-644.

Jain, A. M. & J. B. Mehta, "Sulphonamides, Furazolidone and Neomycin in the Treatment of Infectious Diarrhoea of Infancy and Early Childhood", *Indian Pediatrics*, vol. 6, No. 10 (Oct., 1969), pp. 680-685.

(List continued on next page)

*Primary Examiner*—Shep K. Rose
*Attorney, Agent, or Firm*—Milton B. Graff, IV; Jack D. Schaeffer; Richard C. Witte

[57] ABSTRACT

A furazolidone dosage unit form comprises the drug furazolidone, a sustained release matrix, and an enteric coating.

15 Claims, No Drawings

OTHER PUBLICATIONS

Palasuntheram, C. & D. S. Wijesekera, "Campylobacter Enteritis in Sri Lanka", *Ceylon Medical Journal*, vol. 27, No. 2 (Jun., 1982), pp. 80–84.

Murphy T. V. & J. D. Nelson, "Five v. Ten Days' Therapy with Furazolidone for Giardiasis", *The American Journal of Diseases of Children*, vol. 137, No. 3 (Mar., 1983), pp. 267–270.

Craft, J. C., T. Murphy & J. D. Nelson, "Furazolidone and Quinacrin–Comparative Study of Therapy for Giardiasis in Children", *The American Journal of Diseases of Children*, vol. 135, No. 2 (Feb., 1981), pp. 164–166.

Prasad, R., P. P. Mathur & G. Majumdar, "Comparative Clinical Trial of Furazolidone Suspension Against Metronidazole Syrup in Giardiasis", *Archives of Child Health*, vol. 22, No. 5 (1980), pp. 108–112.

Nair, K. V., M. P. Sharma, S. Mithal & B. N. Tandon, "Success of Metronidazole and Furazolidone in the Treatment of Giardiasis", *The Journal of the Indian Medical Association*, vol. 72, No. 7 (Apr. 1, 1979), pp. 162–165.

Shukla, M. L., S. V. Solanki, U. R. Kothari & J. J. Oza, "Comparative Study of 75 Cases of Enteric Fever Treated with Chloramphenicol, Furazolidone & Combination of Chloramphenicol & Furazolidone", *Indian Medical Gazette*, vol. 115, No. 8 (Aug., 1981), pp. 262–266.

Kamat, S. A., "Management of Enteric Fever in Children", *The Indian Journal of Pediatrics*, vol. 48 (Mar.–Apr., 1981), pp. 203–209.

Gupta, S. P., T. D. Chugh & P. Kapoor, "A Double Blind Study of Chloramphenicol, Furazolidone and Combination Regimens in Enteric Fevers", *The Journal of the Association of Physicians in India*, vol. 26, No. 7 (Jul., 1978), pp. 573–576.

Punjani, M. K. & J. S. Anand, "A Comparative Study of Chloramphenicol and Furazolidone in the Treatment of Typhoid Fever in Chiildren", *Indian Pediatrics*, vol. XV, No. 9 (Sep., 1978), pp. 769–776.

Misra, N. P., S. C. Jain & R. S. Chachra, "Furazolidone in Typhoid Fever", *Current Medical Practice*, vol. 16, No. 8 (Aug., 1972), pp. 345–349.

Damany, S. J. & C. Bilgi, "A Comparative Trial of Furazolidone and Chloramphenicol in Typhoid Fever", *The Journal of the Indian Medical Association*, vol. 55, No. 4 (Aug. 16, 1970), pp. 131–133.

Karchmer, A. W., G. T. Curlin, M. I. Huq & N. Hirschhorn, "Furazolidone in Paediatric Cholera", *Bulletin of World Health Organization*, vol. 43, No. 3 (1970), pp. 373–378.

Pierce, N. F., J. G. Banwell, R. C. Mitra, G. J. Caranasos, R. I. Keimowitz, J. Thomas & A. Mordal, "Controlled Comparison of Tetracycline and Furazolidone in Cholera", *British Medical Journal*, vol. 3 (Aug. 3, 1978), pp. 277–280.

Fish, C. H. & G. Jones, "Furazolidone in the Treatment of Institutional Shigellosis", *American Journal of Mental Deficiency*, vol. 73, No. 2 (Sept. 1968), pp. 214–217.

Haltalin, K. C. & J. D. Nelson, "Failure of Furazolidone Therapy in Shigellosis", *The American Journal of Diseases of Children*, vol. 123, No. 1 (Jan. 1972), pp. 40–44.

Huanambal, M. A., H. Espejo & W. Flores, "Furazolidone Treatment of Infectious Diarrheas Due to Shigella and Salmonella, Clinical and Bacteriological Evaluation", *Tribuna Medical* (Mexico), No. 2 (Dec. 1980), pp. 25–30.

Synge, H. N., and R. Sharma, "Clinical Trial of 'Furoxone' in Treatment of Intestinal Amoebiasis", *Current Medical Practice*, vol. 11, No. 4 (Apr. 1967), pp. 221–223.

Rao, M. H., "Observations on the Value of Furoxone in the Treatment of Amoebiasis", *Bombay Hospital Journal*, vol. 10, (Oct. 1968), pp. 1–4.

Niazi, S. P. & F. Jabeen, "Clinical Trial on Combination of Furazolidone and Iodochlorhydroxyquinoline (Dependal) in the Treatment of Intestinal Amoebiasis", *Journal of the Pakistan Medical Association*, vol. 24, (Apr. 1974), pp. 79–83.

Bhattacharjee, B. & A. K, Mukherjee, "A Clinical Trial with Furazolidone and Iodochlorhydroxyquinoline in Intestinal Amoebiasis", *Calcutta Medical Journal*, vol. 69, No. 4 (1972), pp. 83–84.

Sethi, J. P. & A. Gupta, "'Dependal'–An Evaluation of its Efficacy in the Treatment of Acute and Chronic Intestinal Amoebiasis", *Antiseptic*, vol. 73, No. 10 (Oct. 1976), pp. 545–548.

4,668,517

FURAZOLIDONE DOSAGE FORM

TECHNICAL FIELD

This invention is concerned with a novel dosage form of furazolidone. More particularly, it is concerned with a dosage unit form of furazolidone that is particularly effective in treating disorders of the lower intestinal tract.

BACKGROUND OF THE INVENTION

Furazolidone has a broad antimicrobial spectrum which covers the majority of gastrointestinal tract pathogens, including *E. coli, Staphylococci, Yersinia, Campylobacter, Vibrio, Proteus, Klebsiella, Aeromonas, Plesiomonas, Salmonella, Shigella, Giardia lamblia*, and *Entamoeba histolytica*. Information concerning the antimicrobial activity of furazolidone is provided in the following exemplary references: Rogers, G. S., G. B. Belloff, M. F. Paul, J. A. Yurchenco & G. Gever, "Furazolidone, a New Antimicrobial Nitrofuran", *Antibiotics and Chemotherapy*, Vol. VI, No. 3 (March, 1956), pp. 231-242; Carlson, J. R., S. A. Thornton, H. L. DuPont, A. H. West & J. J. Mathewson, "Comparative In Vitro Activities of Ten Antimicrobial Agents Against Bacterial Enteropathogens", *Antimicrobial Agents and Chemotherapy*, Vol. 24, No. 4 (October, 1983), pp. 509-513; Benazet, F., L. LaCroix, C. Godard, L. Guillaume & J.-P. Leroy, "Laboratory Studies of the Chemotherapeutic Activity and Toxicity of Some Nitroheterocycles", *Scandanavian Journal of Infective Diseases*, Vol. 2, No. 2 (1970), pp. 139-143; Sargeaunt, P. G. & W. H. R. Lumsden, "In Vitro Sensitivity of *Entamoeba histolytica* to Furazolidone and Idochlorhydroxyquin, Separate and Combined", *Transactions of the Royal Society of Tropical Medicine and Hygiene*, Vol. 70, No. 1 (1976), pp. 54-56; Vanhoof, R., H. Goossens, H. Coignau, G. Stas & J. P. Butzler, "Susceptibility Pattern of *Campylobacter jejuni* from Human and Animal Origins to Different Antimicrobial Agents", *Antimicrobial Agents and Chemotherapy*, Vol. 21, No. 6 (June, 1982), pp. 990-992; Lang, W.-L. L. L., B. Reller & M. J. Blaser, "Comparison of Antimicrobial Susceptibility Patterns of *Campylobacter jejuni* and *Campylobacter coli*", *Antimicrobial Agents and Chemotherapy*, Vol. 26, No. 3 (September, 1984), pp. 351-353; Gross, R. J., L. R. Ward, E. J. Threlfall, H. King & B. Rowe, "Drug Resistance Among Infantile Enteropathogenic *Escherichia coli* Strains Isolated in the United Kingdom", *British Medical Journal*, Vol. 285, No. 6340 (Aug. 14, 1982), pp. 472-473; Gross, R. J., E. J. Threlfall, L. R. Ward & B. Rowe, "Drug Resistance in *Shigella dysenteriae, S. flexneri* and *S. boydii* in England and Wales: Increasing Incidents of Resistance to Trimethoprim", *British Medical Journal*, Vol. 288, No. 6419 (Mar. 10, 1984), pp. 784-786; Penhotra, B. R. & B. Desai, "Resistant *Shigella dysenteriae*", *Lancet*, Vol. 2, No. 8364 (December 17, 1983), p. 1420; Saxena, S. N., M. L. Mago, S. Ahuja & H. Singh, "In Vitro Sensitivity of Salmonella Strains Isolated in 1978 to Ampicillin, Chloramphenicol and Furazolidone", *The Indian Journal of Medical Science*, Vol. 35, No. 7 (July, 1981), pp. 147-152; Agrawal, R., O. P. Ghai, Shriniwas, C. G. Domah & V. K. Paui, "Enterotoxigenic Klebsiella Associated Diarrhea in Children", *Indian Pediatrics*, Vol. XVII, No. 9 (September, 1980), pp. 733-737; Agarwal, S. K., V. K. Srivastava, G. C. Upadhyay, G. K. Malik & L. Tewari, ∓Shigellosis in Infants and Children", *Indian Pediatrics*, Vol. 18, No. 5 (May, 1981), pp. 305-310; and Purohit, R. P., K. R. Joshi, M. C. Vyas & K. Banerjee, "Bacteriological Study of Acute Diarrhoeal Disorders in Adults in Jodhpur", *Rajasthan Medical Journal*, Vol. XVIII, No. 4 (October, 1979), pp. 237-246.

Because it is poorly absorbed from the intestinal tract, furazolidone has been shown to be effective in the treatment of several enteric diseases such as giardiasis, cholera, shigellosis, traveler's diarrhea, salmonellosis, and typhoid fever. Furazolidone is effective in the treatment of diarrhea and enteritis caused by organisms primarily affecting the small intestine: for example, *Giardia lamblia, Salmonella typhi,* enterotoxigenic *E. coli* and *Vibrio cholerae*. Publications which report the use of furazolidone in the treatment of these various disorders include the following: DuPont, H. L., C. D. Ericsson, E. Galindo, L. V. Wood, D. Morgan, J. A. M. Bitsura and J. G. Mendiola, "Furazolidone Versus Ampicillin in the Treatment of Traveler's Diarrhea", *Antimicrobial Agents and Chemotherapy*, Vol. 26, No. 2 (August, 1984), pp. 160-163; Turner, A. C., "Traveler's Diarrhoea: Prevention by Chemoprophylaxis", *Scandanavian Journal of Gastroenterology*, Vol. 84, Supplement (1983), pp. 107-110; Lexomboon, U., "Antimicrobial Therapy in Diarrhoeal Diseases in Children", *Southeast Asian Journal of Tropical Medicine and Public Health*, Vol. 13, No. 3 (September, 1982), pp. 418-423; Gupta, S., S. Saxena & G. Srivastava, "Comparative Clinical Trial of Anti-Diarrhoeal Drugs", *Indian Pediatrics*, Vol. XIV, No. 8 (1977), pp. 639-644; Jain, A. M. & J. B. Mehta, "Sulphonamides, Furazolidone and Neomycin in the Treatment of Infectious Diarrhoea of Infancy and Early Childhood", *Indian Pediatrics*, Vol. 6, No. 10 (October, 1969), pp. 680-685; Palasuntheram, C. & D. S. Wijesekera, "Campylobacter Enteritis in Sri Lanka", *Ceylon Medical Journal*, Vol. 27, No. 2 (June, 1982), pp. 80-84; Murphy, T. V. & J. D. Nelson, "Five v. Ten Days' Therapy with Furazolidone for Giardiasis", *The American Journal of Diseases of Children*, Vol. 137, No. 3 (March, 1983), pp. 267-270; Craft, J. C., T. Murphy & J. D. Nelson, "Furazolidone and Quinacrin—Comparative Study of Therapy for Giardiasis in Children", *The American Journal of Diseases of Children*, Vol. 135, No. 2 (February, 1981), pp. 164-166; Presad, R., P. P. Mathur & G. Majumdar, "Comparative Clinical Trial of Furazolidone Suspension Against Metronidazole Syrup in Giardiasis", *Archives of Child Health*, Vol. 22, No. 5 (1980), pp. 108-112; Nair, K. V., M. P. Sharma, S. Methal & B. N. Tandon, "Successes of Metronidazole and Furazolidone in the Treatment of Giardiasis", *The Journal of the Indian Medical Association*, Vol. 72, No. 7 (Apr. 1, 1979), pp. 162-165; Shukla, M. L., S. V. Silanki, U. R. Kothari & J. J. Oza, "Comparative Study of 75 Cases of Enteric Fever Treated with Chloramphenicol, Furazolidone & Combination of Chloramphenicol & Furazolidone", *Indian Medical Gazette*, Vol. 115, No. 8 (August, 1981), pp. 262-266; Kamat, S. A., "Management of Enteric Fever in Children", *The Indian Journal of Pediatrics*, Vol. 48 (March-April, 1981). pp. 203-209; Gupta, S. P., T. D. Chugh & P. Kapoor, "A Double Blind Study of Chloramphenicol, Furazolidone and Combination Regimens in Enteric Fevers", *The Journal of the Association of Physicians in India*, Vol. 26, No. 7 (July, 1978), pp. 573-576; Punjani, M. K. & J. S. Anand, "A Comparative Study of Chloramphenicol and Furazolidone in the Treatment of Typhoid Fever in Children", *Indian Pediatrics*, Vol.

XV, No. 9 (September, 1978), pp. 769–776; Misra, N. P., S. C. Jain & R. S. Chachra, "Furazolidone in Typhoid Fever", *Current Medical Practice*, Vol. 16, No. 8 (August, 1972), pp. 345–349; Damany, S. J. & C. Bilgi, "A Comparative Trial of Furazolidone and Chloramphenicol in Typhoid Fever", *The Journal of the Indian Medical Association*, Vol. 55, No. 4 (Aug. 16, 1970), pp. 131–133; Karchmer, A. W., G. T. Curlin, M. I. Huq & N. Hirschhorn, "Furazolidone in Paediatric Cholera", *Bulletin of World Health Organization*, Vol. 43, No. 3 (1970), pp. 373–378; and Pierce, N. F., J. G. Banwell, R. C. Mitra, G. J. Caranasos, R. I. Keimowitz, J. Thomas & A. Mordal, "Controlled Comparison in Tetracycline and Furazolidone in Cholera", *British Medical Journal*, Vol. 3, (Aug. 3, 1968), pp. 277–280.

The effectiveness of furazolidone in the treatment of diseases affecting the colon and rectum, for example shigellosis and amoebiasis, is inconsistent. The results of studies involving the treatment of such diseases with furazolidone are provided in the following publications; Fish, C. H. & G. Jones, "Furazolidone in the Treatment of Institutional Shigellosis", *American Journal of Mental Deficiency*, Vol. 73, No. 2 (September, 1968), pp. 214–217; Haltalin, K. C. & J. D. Nelson, "Failure of Furazolidone Therapy in Shigellosis", *The American Journal of Diseases of Children*, Vol. 123, No. 1 (January, 1972), pp. 40–44; Huanambal, M. A., H. Espejo & W. Flores, "Furazolidone Treatment of Infectious Diarrheas Due to Sigella and Salmonella. Clinical and Bacteriological Evaluation", *Tribuna Medical* (Mexico), No. 2 (December, 1980), pp. 25–30; Synge, H. N., and R. Sharma, "Clinical Trial of 'Furoxone' in Treatment of Intestinal Amoebiasis", *Current Medical Practice*, Vol. 11, No. 4 (April, 1967), pp. 221–223; Rao, M. H., "Observations on the Value of Furoxone in the Treatment of Amoebiasis", *Bombay Hospital Journal*, Vol. 10 (October, 1968), pp. 1–4; Niazi, S. P. & F. Jabeen, "Clinical Trial on Combination of Furazolidone and Iodochlorhydroxyquinoline (Dependal) in the Treatment of Intestinal Amoebiasis", *Journal of the Pakistan Medical Association*, Vol. 24 (April, 1974), pp. 79–83; Bhattacharjee, B. & A. K. Mukherjee, "A Clinical Trial with Furazolidone and Iodochlorhydroxyquinoline in Intestinal Amoebiasis", *Calcutta Medical Journal*, Vol. 69, No. 4 (1972), pp. 83–84; and Sethi, J. P. & A. Gupta, "'Dependal'—An Evaluation of Its Efficacy in the Treatment of Acute and Chronic Intestinal Amoebiasis". *Antiseptic*, Vol. 73, No. 10 (October, 1976), pp. 545–548.

Furazolidone commonly is administered orally either in liquid suspension or solid dosage form. Common solid dosage forms include capsules and tablets formulated to provide rapid release of the furazolidone in the intestinal tract. A sustained release dosage unit form of furazolidone in the intestinal tract. A sustained release dosage unit form of furazolidone and tylosin for the tratment of pneumoenteritis in calves is disclosed in U.S. Pat. No. 3,790,669 issued to Gale on Feb. 5, 1974. Tablets of furazolidone which may contain certain ingredients and may be film coated which are used for treatment of diseases in which various species of free-living amoeba are the aetiological agent of the disease are disclosed in U.S. Pat. No. 4,402,965 issued to Wyburn-Mason on Sept. 6, 1983.

SUMMARY OF THE INVENTION

It is an object of the present invention to provide novel dosage unit forms of furazolidone which are useful in the treatment of microbial disorders of the lower intestinal tract, especially the colon and rectum.

It is a further object of the present invention to provide such dosage unit forms which are released substantially only in the intestinal tract.

It is a still further object of the present invention to provide such dosage unit forms which result in a sustained release of furazolidone throughout a substantial portion of the entire intestinal tract, such that the furazolidone is present in the lower intestinal tract, especially the colon and rectum, at a sufficient concentration to eradicate microbial pathogens present therein.

It is also an oject of the present invention to provide a novel method for treating microbial disorders of the lower intestinal tract, especially the colon and rectum.

The present invention involves a pharmaceutical dosage unit form comprising:

(a) an effective but nontoxic amount of the drug furazolidone, or its pharmaceutically acceptable salts or hydrates;

(b) a sustained release matrix; and (c) an enteric coating.

DETAILED DESCRIPTION OF THE INVENTION

The present invention relates to novel dosage unit forms of furazolidone, 3-(5-nitrofurfurylideneamino)-2-oxazolidinone having the chemical structure:

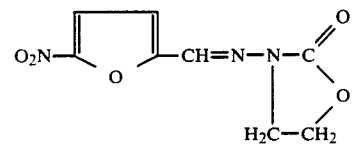

Furazolidone and a method for making it are disclosed in U.S. Pat. No. 2,742,462 issued to Gever on Apr. 17, 1956, which is incorporated herein by reference.

The present invention involves the incorporation of furazolidone in a sustained release matrix. The sustained release matrixes which are useful in the present invention are materials which are insoluble or only slightly soluble in the fluids of the intestinal tract. The preferred sustained release matrixes useful in the present invention are erosible materials which are slowly eroded from the surface of the dosage unit form as it passes through the intestinal tract. Examples of preferred materials useful in forming sustained release matrixes for the present invention include the following: carbomers, methacrylic acid/methyl methacrylate copolymers, methylcellulose, carboxymethylcellulose or its sodium salts, hydroxypropyl methylcellulose, hardened fats such as hydrogenated reposed palm kernel or other vegetable oils, fatty acids and their alkaline salts, polyvinyl chloride, polyvinyl pyrrolidone, and combinations of these materials.

Preferred pharmaceutical dosage unit forms of the present invention comprise furazolidone incorporated substantially uniformly throughout a sustained release matrix which is produced by conventional pharmaceutical tableting techniques. In producing such tablets, furazolidone is blended with one or more of the sustained release materials described hereinabove. Other excipients (pharmaceutical adjuvants) may be added to provide a tablet having the desired erosible characteristics. Excipients incorporated in the tablet may include one or more of the following: (1) fillers to add bulk and to improve compressibility, e.g., lactose, starches, sugars, cellulose derivatives, calcium sulfate or phosphate; (2) binders to form granules or to improve compressibility, e.g., gums, sugars, starch, cellulose derivatives, alginates; (3) lubricants to reduce friction, e.g., stearic acid, metallic stearates, high melting point waxes, talc; and (4) glidants to improve flow, e.g., starch, talc, silica.

Tablets of the present invention which incorporate furazolidone in a sustained release matrix preferably contain from about 10% to about 70% furazolidone. Such tablets preferably comprise one of the preferred sustained release materials in quantities as follows: carbomer preferably within the range of from about 5% to about 40%, more preferably within the range of from about 15% to about 30%; methacrylic acid/methyl methacrylate copolymers preferably within the range of from about 10% to about 15%; methylcellulose preferably within the range of from about 5% to about 10%; carboxymethylcellulose or its sodium salts preferably within the range of from about 5% to about 20%; hydroxypropyl methylcellulose preferably within the range of from about 35% to about 70%; hardened fats such as hydrogenated reposed palm kernel or other vegetable oils, fatty acids and their alkaline salts preferably within the range of from about 10% to about 40%; polyvinyl chloride preferably within the range of from about 15% to about 30%; or polyvinyl pyrrolidone preferably within the range of from about 10% to about 25%.

The pharmaceutical dosage unit forms of the present invention are enteric coated in order to prevent release of the furazolidone in the stomach. The enteric coating is formulated such that it dissolves after the dosage form reaches the intestines in order to expose the sustained release matrix containing the furazolidone to eroding forces in the intestines;

Enteric coating materials which preferably are used as primary ingredients in the enteric coatings of the dosage unit forms of the present invention include the following: polyvinylacetate phthalate, shellac, cellulose acetate phthalate, and polymethacrylate. Especially preferred for the dosage unit forms of the present invention are enteric coatings comprising polyvinylacetate phthalate.

The enteric coatings of the dosage unit forms of the present invention preferably are applied to the tablets comprising furazolidone and sustained release materials described hereinabove by standard pharmaceutical coating techniques. The enteric coating preferably comprises from about 5% to about 10% of the compressed tablet weight. The enteric coating typically is applied by coating the tablet with a fluid mixture comprising the enteric coating material and one or more excipients, such as polyethylene glycol and pigments, and then drying the coating.

In order to improve the uniformity and adhesion of the enteric coating, subcoats of excipients, e.g., a mixture of hydroxypropyl methylcellulose and polyethylene glycol, can be applied to the tablet and dried prior to application of the enteric coating. Polish and/or color coats may be applied to the enteric coated tablet by coating it with excipients, e.g., mixtures of hydroxypropyl methylcellulose, propylene glycol, and pigments, and drying.

The following example describes the preparation of an enteric coated sustained release dosage unit form of furazolidone of the present invention.

EXAMPLE

| Ingredient Weight Per Tablet | Ingredient | Percentage |
| --- | --- | --- |
| 400 mg | furazolidone | 57.1 |
| 105 mg | carbomer 934P | 15.0 |
| 35.9 mg | stearic acid | 5.1 |
| 153.1 mg | sucrose | 21.9 |
| 6.0 mg | zinc stearate | 0.9 |

The ingredients in the above table are mixed according to acceptable pharmaceutical manufacturing practices. The finished blend is screened and convex, capsule-shaped tablets are compressed by direct compression using a suitable tablet press yielding tablets approximately 8 mm in width, 14 mm in length, and 6 mm in height.

The compressed tablets are coated by conventional pharmaceutical manufacturing practices using an Aeromatic fluid bed coater, model STREA-1, marketed by Aeromatic, Inc. of Towaco, NJ. A subcoat is applied to the compressed tablets by applying a 5% aqueous solution of Opadry YS-2-7013 and drying in the coater. (Opadry is supplied by Colorcon, Inc., West Point, PA, and comprises hydroxypropyl methylcellulose and polyethylene glycol.) The subcoated tablets are enteric coated by applying an aqueous solution of 12.5% Coateric Y-PA-6-2427 and 0.13% ammonium hydroxide and drying in the coater. (Coateric is also supplied by Colorcon, Inc., and comprises polyvinylacetate phthalate, polyethylene glycol, titanium dioxide, D&C yellow #10 Alumininum Lake, FD&C yellow #10 Aluminum Lake, sodium alginate and silica.) The enteric coating on each tablet is from about 35 mg to about 70 mg in weight. The enteric coated tablets are polish coated by applying a 5% aqueous solution of Opadry YS-2-7013 and drying in the coater.

Another aspect of the present invention involves a method for treating microbial disorders of the lower intestinal tract, especially the colon and/or rectum, which comprises oral administration of the pharmaceutical dosage unit forms described hereinabove. It has been determined that in the treatment of diseases affecting the colon and rectum, e.g. certain forms of shigellosis, amoebiasis, campylobacteriosis, and salmonellosis, that the administration of conventional oral dosage forms of furazolidone produces inconsistent therapeutic results. This is believed to be due to the fact that a therapeutic dose of the furazolidone orally administered by conventional means fails to reach the colon and rectum because a substantial portion is decomposed in the stomach and/or upper intestinal tract. It is believed that the pharmaceutical dosage unit forms of the present invention, when administered orally, result in the achievement of therapeutic levels of furazolidone in the colon and rectum, such that the furazolidone is able to eradicate microbial pathogens which are there.

In order to achieve clinical success in the treatment of such disorders of the lower intestinal tract with conventional dosage unit forms of furazolidone, it often is necessary to require doses of as much as 200 mg furazolidone four times a day. Such dose of furazolidone frequently is associated with side effects of nausea and vomiting. The pharmaceutical dosage unit forms of the present invention can effectively reduce such side effects by (1) reducing the daily dosage required to eradicate the pathogens and/or (2) by eliminating the release of a large bolus of furazolidone in the stomach and/or the intestines.

With the dosage unit forms of the present invention, the furazolidone is released over a substantial period of time rather than in a large bolus shortly after administration. Therefore, the amount of furazolidone contained in a single dose can usuallly be greater without resulting in adverse side affects. Also, the dosage unit forms of the present invention can be administered less frequently than conventional furazolidone dosage unit forms. Preferred dosage unit forms of the present invention comprise from about 50 mg to about 800 mg of furazolidone, more preferably from about 200 mg to about 400 mg furazolidone. The dosage unit forms of the present invention preferably are administered once to four times daily, more preferably once to twice daily.

The preferred daily dosage of furazolidone using the pharmaceutical dosage unit forms of the present invention is from about 100 mg to about 1200 mg furazolidone per day, especially preferred is from about 400 mg to about 800 mg furazolidone per day.

While particular embodiments of the present invention have been described, it will be obvious to those skilled in the art that various changes and modifications of the dosage unit forms of the present invention and the methods for treating disorders of the colon and rectum can be made without departing from the spirit and scope of the invention. It is intended to cover, in the appended claims, all such modifications that are within the scope of this invention.

What is claimed is:

1. A pharmaceutical dosage unit form for oral administration and for treatment of microbial disorders of the colon and/or rectum, said dosage unit form being a coated tablet comprising a compressed tablet comprising:
   (a) an active drug ingredient consisting of from about 50 mg to about 800 mg furazolidone, or its pharmaceutically acceptable salts or hydrates; and
   (b) a sustained release matrix comprising a material selected from the group consisting of carbomer, methacrylic acid/methyl methacrylate copolymer, methylcellulose, carboxymethylcellulose or its sodium salts, hydroxypropyl methylcellulose, hardened fats, polyvinylchloride, and polyvinyl pyrrolidone;
   said compressed tablet being coated with an enteric coating which is from about 5% to about 10% of the weight of said compressed tablet and comprises a material selected from the group consisting of polyvinylacetate phthalate, shellac, cellulose acetate phthalate, and polymethacrylate.

2. The pharmaceutical dosage unit form of claim 1 wherein said sustained release matrix comprises a carbomer.

3. The pharmaceutical dosage unit form of claim 2 wherein said carbomer is carbomer 934P.

4. The pharmaceutical dosage unit form of claim 1 wherein said enteric coating comprises polyvinylacetate phthalate.

5. The pharmaceutical dosage unit form of claim 2 wherein said enteric coating comprises polyvinylacetate phthalate.

6. The pharmaceutical dosage unit form of claim 1 wherein said dosage unit form comprises from about 200 mg to about 400 mg furazolidone.

7. The pharmaceutical dosage unit form of claim 5 wherein said dosage unit form comprises from about 200 mg to about 400 mg furazolidone.

8. A method for treating microbial disorders of the colon and/or rectum comprising oral administration of the pharmaceutical dosage unit form of claim 1.

9. A method for treating microbial disorders of the colon and/or rectum comprising oral administration of the pharmaceutical dosage unit form of claim 2.

10. A method for treating microbial disorders of the colon and/or rectum comprising oral administration of the pharmaceutical dosage unit form of claim 5.

11. The method of claim 8 wherein said disorder is shigellosis.

12. The method of claim 8 wherein said disorder is amoebiasis.

13. The method of claim 8 wherein said disorder is salmonellosis.

14. The method of claim 8 wherein said disorder is campylobacteriosis.

15. The method of claim 8 wherein said dosage unit form is administered once or twice daily.

* * * * *